(12) United States Patent
Matoba

(10) Patent No.: US 8,596,866 B2
(45) Date of Patent: Dec. 3, 2013

(54) X-RAY TRANSMISSION INSPECTION APPARATUS AND X-RAY TRANSMISSION INSPECTION METHOD

(75) Inventor: Yoshiki Matoba, Chiba (JP)

(73) Assignee: SII NanoTechnology Inc. (JP)

( * ) Notice: Subject to any disclaimer, the term of this patent is extended or adjusted under 35 U.S.C. 154(b) by 333 days.

(21) Appl. No.: 12/932,122

(22) Filed: Feb. 17, 2011

(65) Prior Publication Data

US 2011/0222656 A1 Sep. 15, 2011

(30) Foreign Application Priority Data

Mar. 15, 2010 (JP) ................................. 2010-058426

(51) Int. Cl.
*A61B 6/08* (2006.01)
(52) U.S. Cl.
USPC ............................................ 378/205; 378/62
(58) Field of Classification Search
USPC .................................. 378/51, 58, 62, 205, 207
See application file for complete search history.

(56) References Cited

U.S. PATENT DOCUMENTS 7,290,930 B2 * 11/2007 Hoheisel ........................ 378/206
7,737,427 B2 * 6/2010 Kito et al. ..................... 250/580

OTHER PUBLICATIONS

Patent Abstracts of Japan, publication No. 2001-091480, publication date Apr. 6, 2001.

* cited by examiner

*Primary Examiner* — Jurie Yun
(74) *Attorney, Agent, or Firm* — Adams & Wilks

(57) ABSTRACT

To prevent erroneous detection in detecting a foreign matter, which is caused by a change in distance between a sample and an X-ray detector, provided is an X-ray transmission inspection apparatus including an X-ray tube (11) that irradiates an inspection sample element with an X-ray, an X-ray detector (13) that detects a transmission X-ray when the X-ray is transmitted through a sample, an operation portion (17) that obtains a contrast image from a transmission image of a transmission X-ray, a sensor that calculates a distance between the sample and the detector, and a mechanism that adjusts the position of the X-ray detector, in which an X-ray transmission image is picked up while the distance between the sample and the X-ray detector is kept constant.

16 Claims, 3 Drawing Sheets

F I G. 1
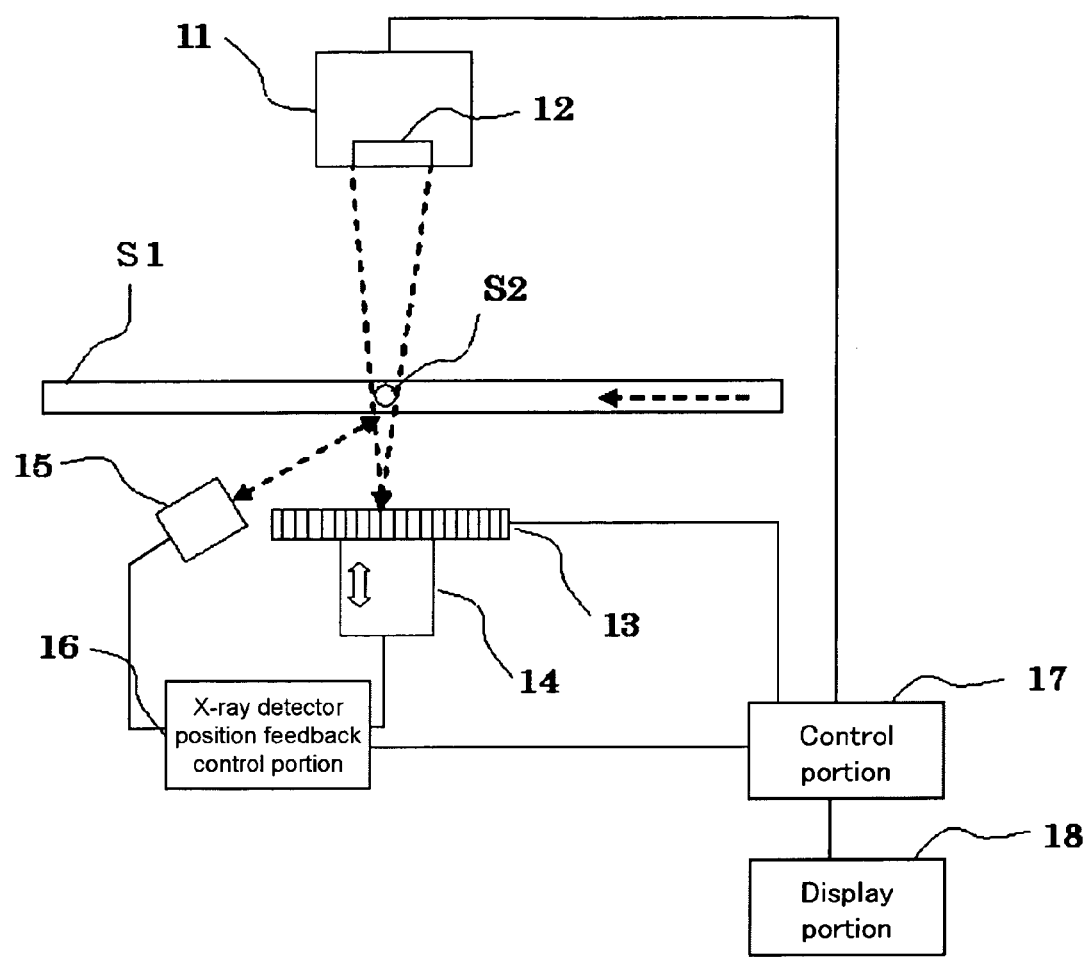

F I G . 2
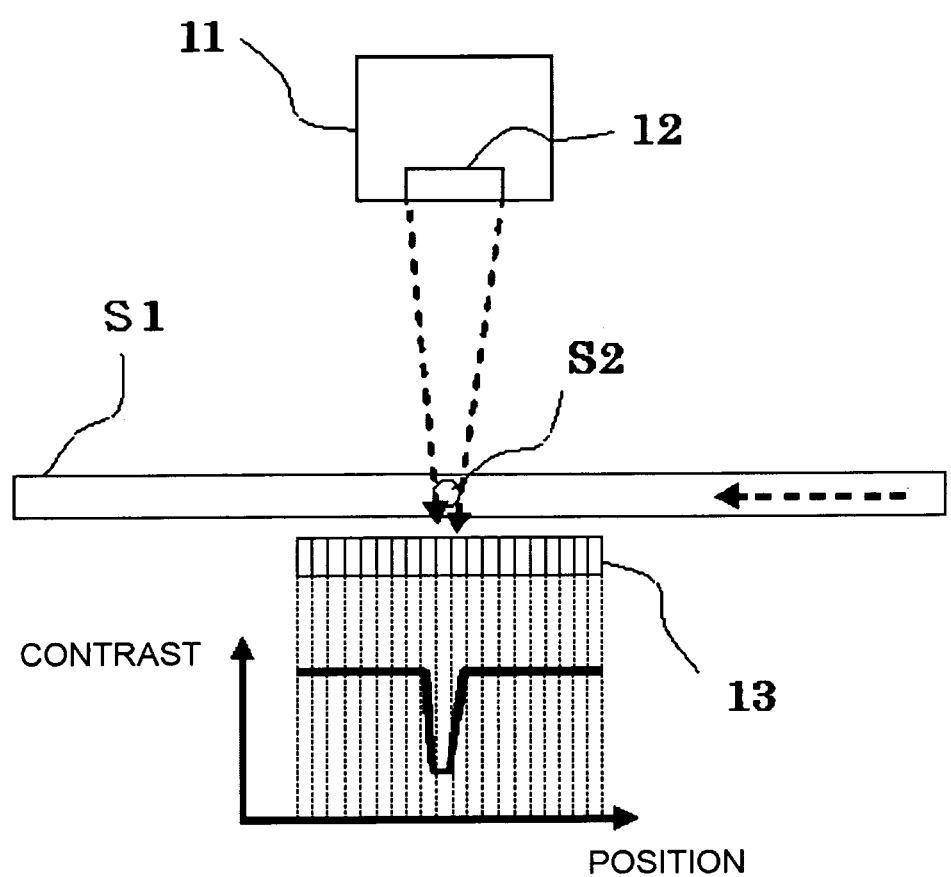

X-RAY TRANSMISSION INSPECTION APPARATUS AND X-RAY TRANSMISSION INSPECTION METHOD

BACKGROUND OF THE INVENTION

1. Field of the Invention

The present invention relates to an X-ray transmission inspection apparatus and an X-ray transmission inspection method which are capable of detecting a foreign matter formed of a particular element in a sample.

2. Description of the Related Art

In recent years, a lithium-ion secondary battery, which has a higher energy density compared with that of a nickel-metal hydride battery, has been increasingly adopted as a battery for an automobile, a hybrid car, an electric vehicle, and the like. The lithium-ion secondary battery is a kind of a non-aqueous electrolyte secondary battery, which has lithium ions in an electrolyte conducting electricity and does not contain metal lithium, and has already been used widely in notebook personal computers and mobile phones.

The lithium-ion secondary battery has excellent battery characteristics. However, when a foreign matter such as Fe (iron) enters in an electrode during a production process, the reliability of the battery is adversely affected, such as degradation in battery characteristics as to a heat-generation property, a longevity, and the like, which has delayed installation of the battery on a vehicle. For example, an electrode (anode) of the lithium-ion secondary battery is generally formed in such a manner that a lithium manganese oxide film or a lithium cobalt oxide film is formed to have a thickness of about 100 μm on both surfaces of an Al film having a thickness of 20 μm. A foreign matter such as Fe (iron) or SUS (stainless) may be mixed into the electrode, and if the size of the foreign matter is tens of μm or larger, short-circuit occurs, and may cause burning of the battery and decrease in performance. Therefore, there is a demand in the lithium-ion secondary battery that a battery with a foreign matter X mixed therein during production be detected swiftly and the foreign matter X be removed in advance.

In general, as a method of detecting a foreign matter or the like in a sample, a method using a transmitted X-ray image is known. Using this procedure, for example, as disclosed in Japanese Unexamined Patent Application Publication No. 2001-91480 (in claims), a method of detecting a presence/absence of foreign matter through the transmitted X-ray image has been proposed conventionally.

The above-mentioned related art has the following problem.

That is, according to a conventional method of detecting a foreign matter, clearness of an image of a foreign matter varies between the case where the position of the foreign matter is close to an X-ray detector and the case where the foreign matter is far away from the X-ray detector. Therefore, according to the conventional method of detecting a foreign matter, a large difference in contrast caused by the foreign matter occurs between the case where the foreign matter is close to the X-ray detector as illustrated in FIG. 2 and the case where the foreign matter is far away from the X-ray detector as illustrated in FIG. 3, and an image to be taken varies even with a foreign matter of the same size and the same material. This leads to a problem such as overdetection or erroneous detection.

SUMMARY OF THE INVENTION

The present invention has been achieved in view of the above-mentioned problems, and an object thereof is to provide an X-ray transmission inspection apparatus and an X-ray transmission inspection method capable of faithfully reproducing a contrast of an image caused by a foreign matter of the same size and the same material and thus preventing overdetection and erroneous detection.

The present invention adopts the following configuration so as to solve the above-mentioned problems. More specifically, an X-ray transmission inspection apparatus of the present invention includes an X-ray tube that irradiates an inspection sample with an X-ray, an X-ray detector that receives a transmission X-ray corresponding to the X-ray having transmitted through the inspection sample to detect an intensity thereof, an operation portion that creates a transmission image indicating a distribution of detected intensity of the transmission X-ray, a distance sensor that measures a distance between the inspection sample and the inspection apparatus, and a mechanism for adjusting the distance between the X-ray detector and the inspection sample, placed in the X-ray detector.

Further, an X-ray transmission inspection method of the present invention includes irradiating an inspection sample with an X-ray, measuring a distance between the inspection sample and an inspection apparatus, adjusting a distance between the X-ray detector and the inspection sample in response to a distance measurement result, receiving a transmission X-ray corresponding to the X-ray transmitted through the sample and detecting the intensity thereof, and creating a transmission image indicating a distribution of the detected intensity of the transmission X-ray.

According to the X-ray transmission inspection apparatus and the X-ray transmission inspection method described above, an X-ray transmission image is obtained while the distance between the inspection sample and the X-ray detector is kept constant at all times. Therefore, a contrast caused by the foreign matter in an inspection target may be obtained irrespective of a position of the inspection sample.

According to the present invention, the following effects are exhibited.

That is, according to the X-ray transmission inspection apparatus and the X-ray transmission inspection method of the present invention, even when the distance between the inspection sample and the inspection apparatus varies, the distance between the inspection sample and the X-ray detector can be kept constant by adjusting a position of the X-ray detector based on the distance measurement result, and a transmission X-ray image caused by the foreign matter in the inspection sample can be picked up stably, which enhances the reproducibility of a foreign-matter size and prevents overdetection and erroneous detection in a detection of the foreign matter.

Accordingly, using the X-ray transmission inspection apparatus and the X-ray transmission inspection method, a foreign matter of a particular element in the lithium-ion secondary battery or the like can be detected rapidly with high precision.

BRIEF DESCRIPTION OF THE DRAWINGS

In the accompanying drawings:

FIG. 1 is a schematic entire structural view illustrating an embodiment of an X-ray transmission inspection apparatus and an X-ray transmission inspection method according to the present invention;

FIG. 2 is a schematic view of a contrast obtained during irradiation of an X-ray in a conventional X-ray transmission inspection apparatus and X-ray transmission inspection method.

DETAILED DESCRIPTION OF THE PREFERRED EMBODIMENT

Figure 3:
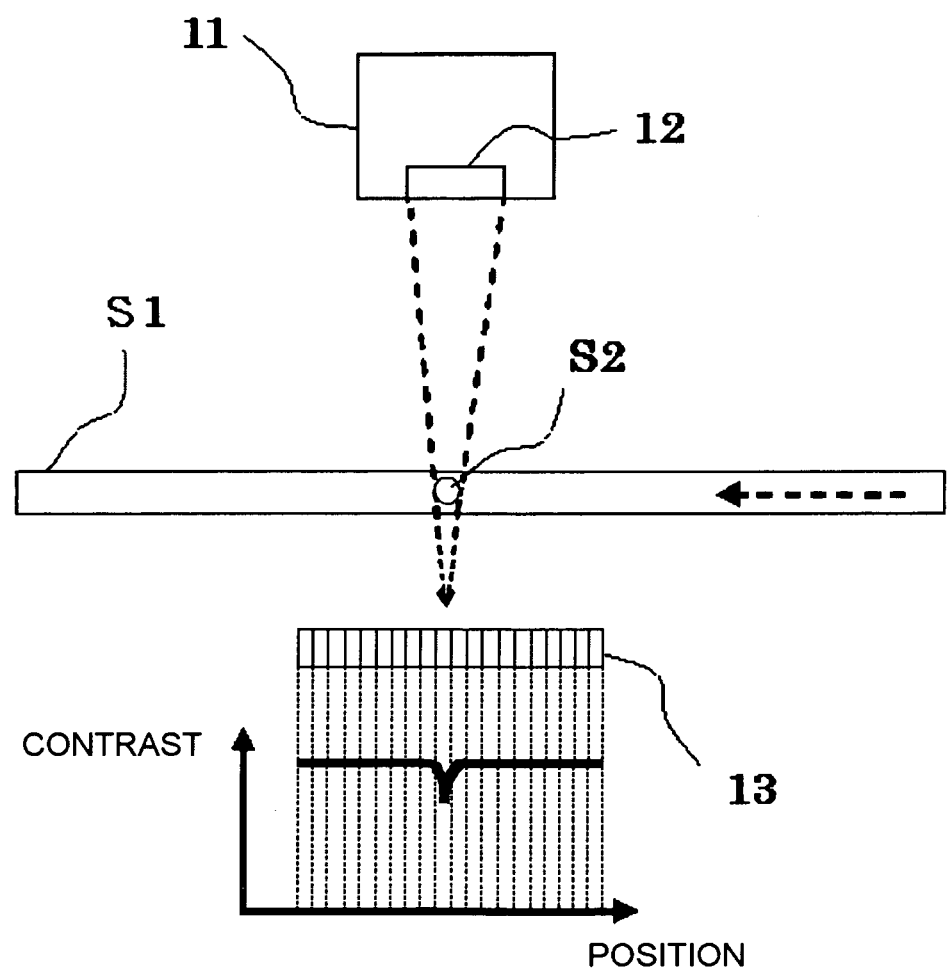
FIG. 3 is a schematic view of another contrast obtained during irradiation of an X-ray in the conventional X-ray transmission inspection apparatus and X-ray transmission inspection method.

Hereinafter, an embodiment of an X-ray transmission inspection apparatus and an X-ray transmission inspection method according to the present invention is described with reference to FIGS. 1 to 3.

As illustrated in FIG. 1, an X-ray transmission inspection apparatus of this embodiment includes an X-ray tube 11 having an X-ray generation point 12 with a certain size, an X-ray detector 13 that receives a transmission X-ray corresponding to the X-ray transmitted through an inspection sample S1 and a foreign matter S2 to detect the intensity thereof, and a display portion 18 that displays a transmission image indicating a distribution of the detected intensity of the transmission X-ray.

Further, the X-ray transmission inspection apparatus includes a distance measurement sensor 15 that measures a distance from the sample S1 to the sensor, an X-ray detector position adjusting mechanism 14 that adjusts a position in a height direction of the X-ray detector 13 based on a measurement result of the distance measurement sensor 15, and an X-ray detector position feedback control portion 16 that performs feedback control thereof.

Further, the X-ray transmission inspection apparatus includes the display portion 18 that is a display device connected to a control portion 17, which is connected to and controls each of the above-mentioned components, and displays the contrast image or the like.

The inspection sample S1 is, for example, an electrode sheet used in a lithium-ion secondary battery, and the foreign matter S2 is, for example, Fe or SUS that may be mixed in the electrode as a foreign matter.

The X-ray tube 11 emits an X-ray, which is generated when thermions generated from a filament (anode) in the tube are accelerated by a voltage applied between the filament (anode) and a target (cathode) to collide against the target, as a primary X-ray from a window of beryllium foil or the like. Generally, a region where the target is irradiated with electrons is the X-ray generation point 12.

The X-ray detector 13 is an X-ray line sensor placed below the sample S1 so as to be opposed to the corresponding X-ray tube 11. As the X-ray line sensor, a scintillator system in which an X-ray is converted into fluorescent light by a fluorescent plate and converted into a current signal by light-receiving elements aligned in a row, a semiconductor system in which a plurality of semiconductor detecting elements are aligned in a row and detected directly, or the like is adopted. Further, the X-ray sensor may be an X-ray area sensor in which light-receiving elements are arranged two-dimensionally, instead of a single-row line.

The control portion 17 is a computer configured by a CPU or the like. The control portion 17 includes an operation processing circuit or the like, which creates a transmission image by image processing based on a signal input from the X-ray detector 13 and caused the display portion 18 to display the image. Further, the display portion 18 is capable of displaying various kinds of information in accordance with the control from the control portion 17.

The distance measurement sensor 15 is placed so as to be opposed to the sample S1, using a reflection-type laser sensor mainly utilizing trigonometry. Distance measurement sensors utilizing other principles, capable of achieving the same object, may be used. The distance measurement result from the distance measurement sensor is sent to the X-ray detector position feedback control portion 16. The X-ray detector position feedback control portion 16 determines that the distance between the sample S1 and the X-ray detector has changed when there is a change in the distance measurement result based on information from the distance measurement sensor 15, and drives the X-ray detector position adjusting mechanism 14 so that the distance between the sample S1 and the X-ray detector 13 becomes substantially constant, i.e., is maintained within a predetermined range. As the X-ray detector position adjusting mechanism 14, various driving mechanisms such as a screw feeder and a linear motor can be applied as long as they are driving mechanisms performing linear drive.

Next, an X-ray transmission inspection method using the X-ray transmission inspection apparatus of this embodiment is described with reference to FIGS. 1 to 3. An object of the X-ray transmission inspection method is to detect the foreign matter, for example, in a positive electrode sheet in the lithium-ion secondary battery as an inspection sample.

First, the sample S1 is caused to flow between the X-ray tube 11 and the X-ray detector 13 opposed to each other in a facility on a production step side (not shown). Thickness of the sample S1 is much smaller compared with the distance between the sample S1 and the X-ray detector 13.

Then, the distance between the sample S1 and the X-ray detector 13 is calculated from a result of the distance measurement sensor 15. In the case where there is a difference between a calculated result of the distance and an initial value D, the X-ray detector position adjusting mechanism 14 is operated, and a difference amount calculated so that the distance between the sample 51 and the X-ray detector 13 becomes the initial value D is fed back by the feedback control portion, and the position of the X-ray detector is adjusted in accordance with the amount. In this case, with the difference between a calculated value of the distance between the sample S1 and the X-ray detector 13, and the initial value D, it is capable of setting a threshold value as an operation determination criterion of the X-ray detector position adjusting mechanism 14.

Next, the sample S1 is irradiated with an X-ray from the X-ray tube 11, and a transmission X-ray having transmitted through the sample S1 and the foreign matter S2 is detected by the X-ray detector 13. At this time, the sample & S1 is moved by the facility on the production step side (not shown), and thus, the entire sample S1 is scanned to obtain an entire intensity distribution regarding the transmission X-ray.

The intensity distribution of the transmission X-ray thus obtained is subjected to image processing by the control portion 17 and thus, a transmission image is created.

At this time, an X-ray transmission amount varies between a site where the foreign matter S2 is present and a site where the foreign matter S2 is not present. Therefore, the contrast of the site where the foreign matter S2 is present is different from that in the other sites as illustrated in FIG. 2. Presence of the foreign matter is detected based on this result.

On the other hand, when the sample S1 moves upward and the distance between the sample S1 and the X-ray detector 13 is increased due to the state of a sample feed device held on the production facility side, a contrast and intensity distribution caused by a foreign matter varies for the reason of the size of the X-ray generation point. As a result, as illustrated in FIG. 3, it is difficult to recognize degree of the contrast caused by the foreign matter and the foreign matter cannot be detected.

Therefore, in the present invention, the distance between the sample S1 and the X-ray detector is measured at all times, using the distance measurement sensor 15. In the case where a difference of a certain value S or more occurs in the distance measurement result with respect to the initial value D, the position of the X-ray detector is adjusted using the X-ray detector position adjusting mechanism 14 appropriately in accordance with the difference so that the distance between the sample S1 and the X-ray detector 13 falls in the initial predetermined range D±S.

Thus, according to the X-ray transmission inspection apparatus and the X-ray transmission inspection method of this embodiment, an X-ray transmission image can be picked up while the distance between the inspection sample and the X-ray detector is kept substantially constant, and thus, a contrast caused by the foreign matter on the X-ray transmission image may be obtained stably. More specifically, a contrast obtained from a foreign matter of the same size and the same material is stable, and hence, the erroneous detection and the overdetection of the foreign matter may be prevented.

Accordingly, a foreign matter of a particular element in a lithium-ion secondary battery or the like can be detected rapidly with high precision, using the X-ray transmission inspection apparatus and the X-ray transmission inspection method.

Further, although the distance measurement sensor 15 is placed on the X-ray detector side in this embodiment, the distance between the sample S1 and the X-ray detector 13 may be calculated even when the distance measurement sensor 15 is placed on the X-ray tube 11 side. It should be noted that the technical scope of the present invention is not limited to the above-mentioned embodiment, and may be variously modified as long as it does not depart from the spirit of the present invention.

What is claimed is:

1. An X-ray transmission inspection apparatus, comprising:
   an X-ray tube that irradiates a moving inspection sample with an X-ray;
   an X-ray detector that receives a transmission X-ray corresponding to the X-ray having transmitted through the moving inspection sample and detects the intensity of the transmission X-ray;
   an operation portion that obtains a contrast image from a transmission image indicating a distribution of the detected intensity of the transmission X-ray;
   a distance measurement portion that measures a distance between the moving inspection sample and the X-ray detector; and
   a distance adjusting mechanism that relatively adjusts the distance between the moving inspection sample and the X-ray detector based on the measured distance to maintain the distance within a predetermined range.

2. An X-ray transmission inspection apparatus according to claim 1, further comprising a feedback control portion that sets, as a feedback amount, a difference amount between a reference distance between the moving inspection sample and the X-ray detector which is set and stored previously, and an actually measured value of the distance measurement portion, and feeds the feedback amount back to the distance adjusting mechanism as an adjustment amount.

3. An X-ray transmission inspection apparatus according to claim 2, wherein the reference distance is a value measured by the distance measurement portion before beginning of measurement or at a time of beginning of measurement.

4. An X-ray transmission inspection apparatus according to claim 1, wherein the distance measurement portion continuously measures the distance between the moving inspection sample and the X-ray detector while the moving inspection sample traverses the X-ray tube and is irradiated with the X-ray.

5. An X-ray transmission inspection method, comprising:
   irradiating a moving inspection sample with an X-ray;
   receiving a transmission X-ray corresponding to the X-ray having transmitted through the moving inspection sample at an X-ray detector and detecting the intensity of the transmission X-ray;
   calculating a distribution of the detected intensity of the transmission X-ray;
   displaying a contrast image based on the calculated intensity distribution;
   measuring a distance between the moving inspection sample and the X-ray detector; and
   adjusting the distance between the moving inspection sample and the X-ray detector based on the measured distance to maintain the distance within a predetermined range.

6. An X-ray transmission inspection method according to claim 5, further comprising feeding back, as an adjustment amount, a difference amount between a reference distance between the moving inspection sample and the X-ray detector which is set and stored previously, and an actually measured value of a distance measurement portion,
   wherein the distance is adjusted by a feedback amount in the adjusting the distance.

7. An X-ray transmission inspection method according to claim 5, wherein the inspection sample is an electrode sheet containing lithium manganese oxide or lithium cobalt oxide.

8. An X-ray transmission inspection method according to claim 5, wherein the distance between the moving inspection sample and the X-ray detector is adjusted by displacing the X-ray detector.

9. An X-ray transmission inspection method according to claim 5, wherein the distance between the moving inspection sample and the X-ray detector is measured continuously as the moving inspection sample traverses the irradiating X-ray.

10. An X-ray transmission inspection apparatus for inspecting a moving sample for the presence of foreign matter, the apparatus comprising:
    an X-ray tube that irradiates a moving sample with an X-ray;
    an X-ray detector positioned to detect the intensity of the X-ray that passes through the moving sample and output a signal representative of the intensity distribution of the X-ray passing through the moving sample;
    means for creating, based on the output signal from the X-ray detector, a contrast image in which foreign matter present in the moving sample is able to be recognized;
    a distance measurement sensor that measures a distance between the X-ray detector and that portion of the moving sample being irradiated with the X-ray; and
    a distance adjusting mechanism that relatively adjusts the distance between the moving sample and the X-ray detector based on the measured distance to maintain the distance within a predetermined range.

11. An X-ray transmission inspection apparatus according to claim 10, further comprising a feedback control portion that feeds an adjustment amount derived from the measurement result of the distance measurement sensor to the distance adjusting mechanism for driving the distance adjusting mechanism to maintain the distance within the predetermined range.

12. An X-ray transmission inspection apparatus according to claim 11, wherein the moving sample contains lithium manganese oxide or lithium cobalt oxide, and the contrast image shows iron or stainless steel as foreign matter present in the moving sample.

13. An X-ray transmission inspection apparatus according to claim 11, wherein the distance adjusting mechanism moves the X-ray detector upward or downward to adjust the distance between the moving sample and the X-ray detector.

14. An X-ray transmission inspection apparatus according to claim 10, wherein the moving sample contains lithium manganese oxide or lithium cobalt oxide, and the contrast image shows iron or stainless steel as foreign matter present in the moving sample.

15. An X-ray transmission inspection apparatus according to claim 10, wherein the distance adjusting mechanism moves the X-ray detector upward or downward to adjust the distance between the moving sample and the X-ray detector.

16. An X-ray transmission inspection apparatus according to claim 10, wherein the distance measurement sensor continuously measures the distance while the moving sample is moving past the X-ray tube and being irradiated with the X-ray.

* * * * *